United States Patent [19]
Johnson et al.

[11] Patent Number: 5,547,470
[45] Date of Patent: *Aug. 20, 1996

[54] AUTOMATED DRUG INFUSION SYSTEM

[75] Inventors: Noel L. Johnson, San Jose; Jyh-Yi T. Huang, Sunnyvale; Robert R. Burnside, Mountain View, all of Calif.

[73] Assignee: Abbott Laboratories, Abbott Park, Ill.

[*] Notice: The term of this patent shall not extend beyond the expiration date of Pat. No. 5,378,231.

[21] Appl. No.: 310,774

[22] Filed: Sep. 27, 1994

Related U.S. Application Data

[63] Continuation of Ser. No. 981,673, Nov. 25, 1992, Pat. No. 5,378,231.

[51] Int. Cl.⁶ .................................................. A61M 31/00
[52] U.S. Cl. .................. 604/67; 604/151; 123/DIG. 12; 123/DIG. 13
[58] Field of Search .................. 128/DIG. 12, DIG. 13; 604/65, 67, 151, 131, 81, 118, 246

[56] References Cited

U.S. PATENT DOCUMENTS

| | | |
|---|---|---|
| 4,513,796 | 4/1985 | Miller et al. |
| 4,533,347 | 8/1985 | Deckert. |
| 4,553,958 | 11/1985 | LeCocq. |
| 4,731,051 | 3/1988 | Fischell. |
| 4,756,706 | 7/1988 | Kerns et al. |
| 4,898,578 | 2/1990 | Rubalcaba, Jr. |
| 5,072,660 | 12/1991 | Helbling. |
| 5,078,683 | 1/1992 | Sancoff et al. |
| 5,100,380 | 3/1992 | Epstein et al. |

OTHER PUBLICATIONS

"Kinetics of Anaesthetic Drugs in Clinical Anesthesiology", *Clinical Anesthesiology International Practice And Research*, P. F. White, pp. 735, 760, 763.
"Intravenous Drug Delivery Systems", *Drug Infusions in Anesthesiology*, P. Glass et al, pp. 23 and 34.
"Lifecare 5000 Plum Infusion System With Concurrent Delivery Feature 2507–04–03/04" System Operating Manual, Abbott Laboratories, N. Chicago, IL, Publication #430–03388–012, Copyright 1990.

*Primary Examiner*—Corrine M. McDermott
*Assistant Examiner*—N. Kent Gring

[57] ABSTRACT

The present invention relates to a control system for use with an automated intravenous drug and fluid infusion system having plural pumping channels that operate independently for intravenously infusing drugs and fluid. The pumping channels are controlled by a microprocessor-based host controller that monitors each of the channels concurrently. In an exemplary embodiment, the system functions include identifying the particular drug that is to be pumped through a channel, preventing priming of a channel unless verification is provided that the channel is not connected to a patient and initiating the priming of each of the pumping channels independently.

8 Claims, 4 Drawing Sheets

AUTOMATED DRUG INFUSION SYSTEM

This application is a continuation of application Ser. No. 07/981,673, filed Nov. 25, 1992 now U.S. Pat. No. 5,378, 231.

BACKGROUND OF THE INVENTION

1. Field of the Invention

The present invention generally relates to systems for delivering drugs and fluids to patients intravenously. More particularly, the present invention relates to a control system for an automated intravenous drug and fluid infusion system.

2. State of the Art

It is well known to use volumetric infusion pumping systems for delivering drugs to patients intravenously. Infusion pumping systems of conventional design have several significant drawbacks that limit their effectiveness. For example, manual entry via keys and knobs is required whenever a drug supply container is connected or replaced in the pumping system. Further, conventional pumping systems require manual identification of drugs and manual priming of pumping channels.

The foregoing manual procedures are time consuming, labor-intensive and susceptible to error. Because there is no procedure for identifying and approving use of a drug in an infusion pumping system, successive use of different drugs in the same delivery line can occur, resulting in drug contamination. Further, the lack of drug identification can result in the mixing of incompatible drugs from plural drug channels.

SUMMARY OF THE INVENTION

The present invention relates to a control system for use with an automated intravenous drug and fluid infusion system having plural pumping channels that operate independently. Each pumping channel is independently controlled by a single microprocessor-based central processing unit (CPU). A host controller monitors all of the channels concurrently. In an exemplary embodiment, the system further includes means for positively identifying the particular drug that is to be pumped through a channel; means for preventing priming of a channel unless verification is provided that the channel is not connected to a patient; and means for independently priming each of the pumping channels.

The present invention provides easy to use methods and systems which improve patient care by automating control during all phases of drug and fluid delivery. The system provides positive identification of drugs prior to their administration via the various pumping channels, and provides autopriming of the channels. Dosing and delivery (i.e., by bolus, continuous infusion, or pharmacokinetic model-based infusion) can be entered in user-selectable units which are internally converted to system units (ml/hr.).

The control system can also recognize incompatible drug combinations, and subsequently handle the incompatibility or alert the device user via an appropriate warning. Automatic dose limit checking, automatic data storage (e.g., patient record, user data and infusion data), and automatic detection and signaling of error conditions represent additional features of the control system.

BRIEF DESCRIPTION OF THE DRAWINGS

The present invention can be further understood with reference to the following description and the appended drawings, wherein like elements are provided with the same reference numerals. In the drawings.

DETAILED DESCRIPTION OF THE PREFERRED EMBODIMENTS

Figure 1:
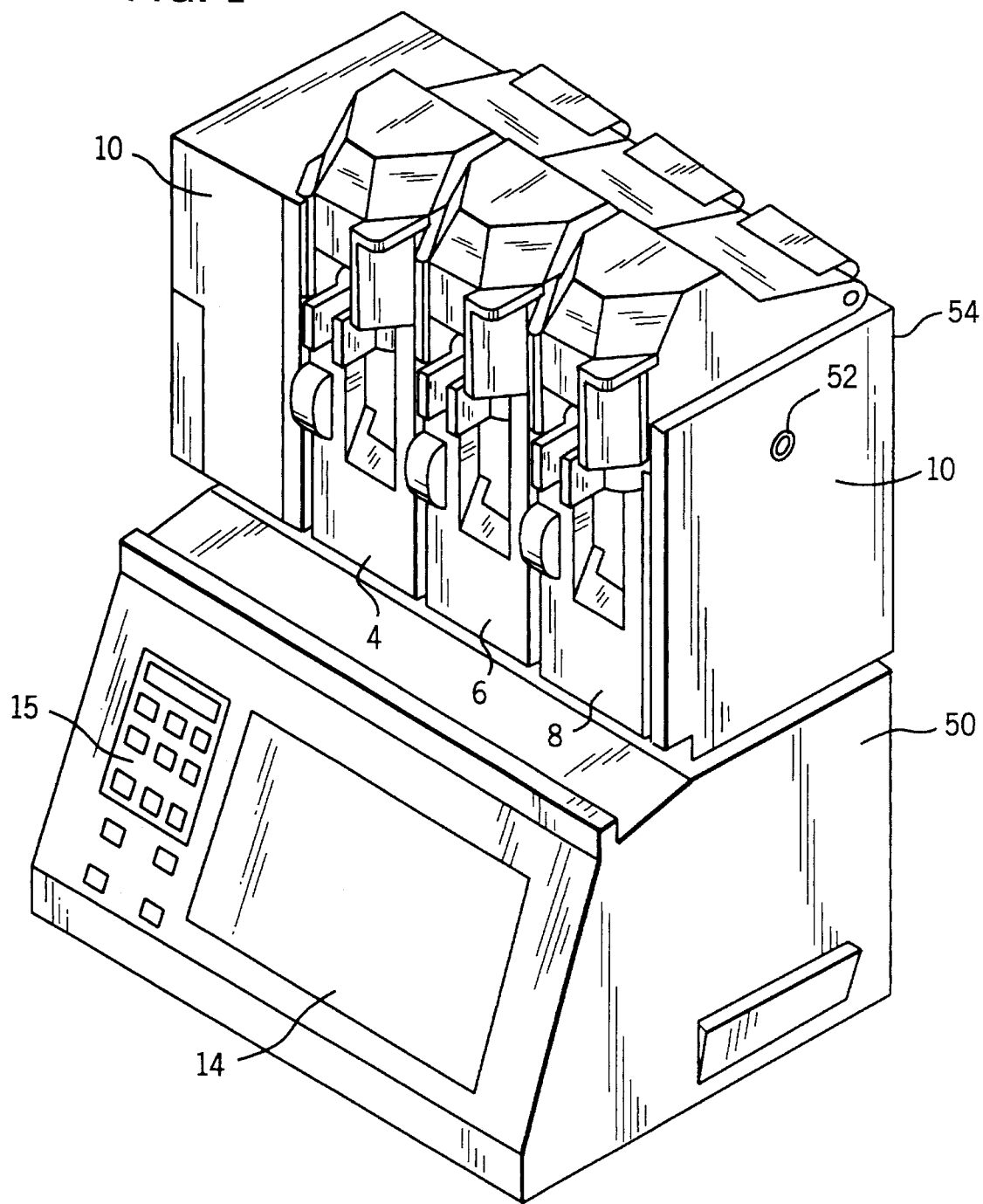
FIG. 1 is an exemplary automated drug infusion (ADI) pumping system of the type that dispenses drugs and fluids to a patient intravenously from one or more drug and fluid supply containers.

FIG. 1 shows an ADI pumping system for dispensing drugs and fluids for a patient intravenously from one or more drug and fluid supply containers. The FIG. 1 apparatus includes three substantially equal drug delivery channels 4, 6 and 8, and a fluid delivery channel 10. Drug delivery parameters are entered and displayed via a touch screen 14. Fluid parameters are entered via a key pad 15. A base enclosure 50 encloses a host controller 2 for driving the overall system. A key lock 52 is disposed on a side of a pumping channel enclosure 54 and engages a security system. Detailed aspects of an exemplary drug identification and security system which can be used with the FIG. 1 apparatus are set forth in commonly assigned U.S. application Ser. No. 07/811,516, entitled "Drug Channel Identification And Security System For Infusion And Pumping Systems" and filed Dec. 20, 1991, the contents of which are hereby incorporated by reference.

Figure 2:
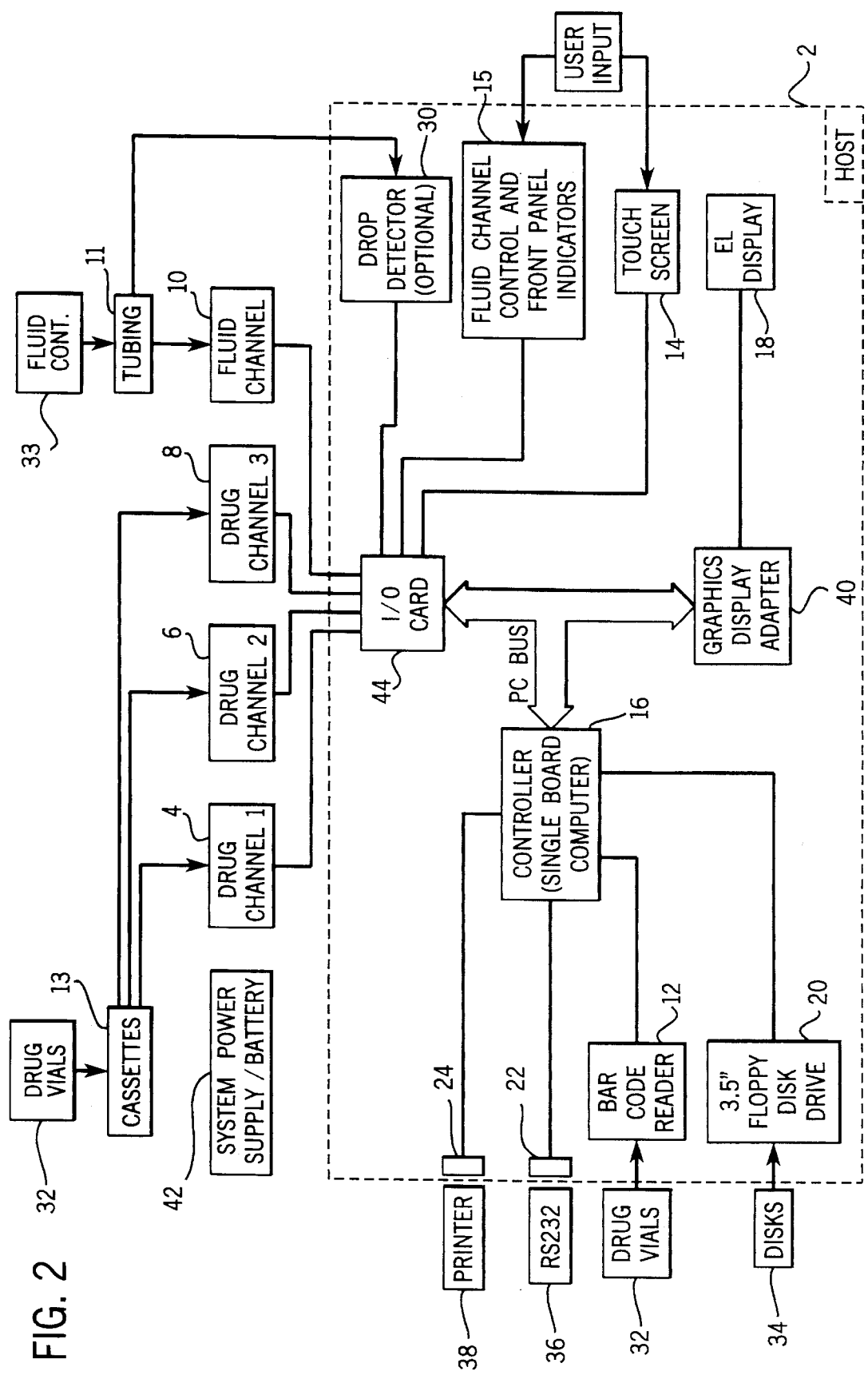
FIG. 2 is a block diagram of a control system for the FIG. 1 pumping system.

FIG. 2 shows a general hardware block diagram of an automated drug and fluid infusion control system for intravenously infusing drugs and fluid to a patient via the FIG. 1 pumping system. The FIG. 2 system includes three general components: a host controller 2; drug channels 4, 6 and 8; and a fluid channel 10.

The FIG. 2 system represents a modular, multi-channel infusion device with each drug channel holding a captive drug vial exclusively compatible with the system and with a drug administration set. A master-slave control approach is used, with the host controller 2 overseeing operation of the four independent pump channel modules: three identical channels for the delivery of drug (e.g., anesthetic and cardiovascular agents), and one channel for fluid delivery.

For purposes of the following discussion, the term "drug channel" refers to an independent path through which drug is dispensed to a patient from at least one drug supply container, or vial 32. In systems according to the present invention, each drug channel includes a cassette pumping device 13. Access to a drug pumping cassette 13 within a drug channel is provided by lifting a protective hood on top of the pumping system. When not in use, the hood or hoods may be locked to prevent removal of the drugs.

Pump outlets in each independent drug channel may be connected to a manifold or connected directly to the patient. The preferred manifold contains four one-way check valves which connect all input lines to an outlet line through which drugs and fluid are dispensed to a patient intravenously, for example, a manifold such as described in commonly assigned U.S. application Ser. No. 07/734,828, entitled "Multi-Valve Manifold For Drug Infusion Systems", filed Jul. 24, 1991.

A "fluid channel" refers to a path through which a fluid (e.g., flushing fluid) is dispensed via the manifold. The FIG. 2 fluid channel 10 can carry fluid such as a patient hydration solution. The fluid channel 10 includes a fluid supply container 33 which is compatible with a conventional drop sensor 30. The drop sensor is connected to fluid conduit 11 that passes through a volumetric fluid channel pump. The fluid channel 10 also connects to the manifold via a one-way check valve.

The host controller 2 is a single microprocessor-based computer which responds to user commands, directs intravenous drug and fluid deliveries, automatically recognizes drug identities, stores and selectively activates a pharmacokinetic (PK) model useful in drug delivery to the patient, handles physical incompatibilities among drugs, and provides automatic record keeping. The host controller 2 includes a microprocessor 16 which monitors and controls the independent pumping channels concurrently. The host controller 2 includes a system user interface which enables the user to identify the drug installed in each drug channel, select infusion modes, set infusion rates, identify drug incompatibilities, prevent priming of a drug channel unless verification is provided that the channel is not connected to a patient, and related functions. Further, the host controller 2 causes automatic priming of each pumping channel independently.

The automatic priming removes air from each of the pump cassettes 13 and associated tubing independently. A discussion of the autoprime feature is provided in commonly assigned U.S. patent application Ser. No. 07/811,195, entitled "Automated Drug Infusion System With Autopriming" filed Dec. 20, 1991. Because an understanding of the auto-prime feature of the system described herein may be useful for a better understanding of the present invention, the above-noted U.S. patent application is herein incorporated by reference.

The FIG. 2 system includes means for identifying the particular drug that is to be pumped through a drug channel. A modular bar code reading system 12 identifies the drug contained in a drug vial 32 installed in a drug channel of the system.

Figure 3A:
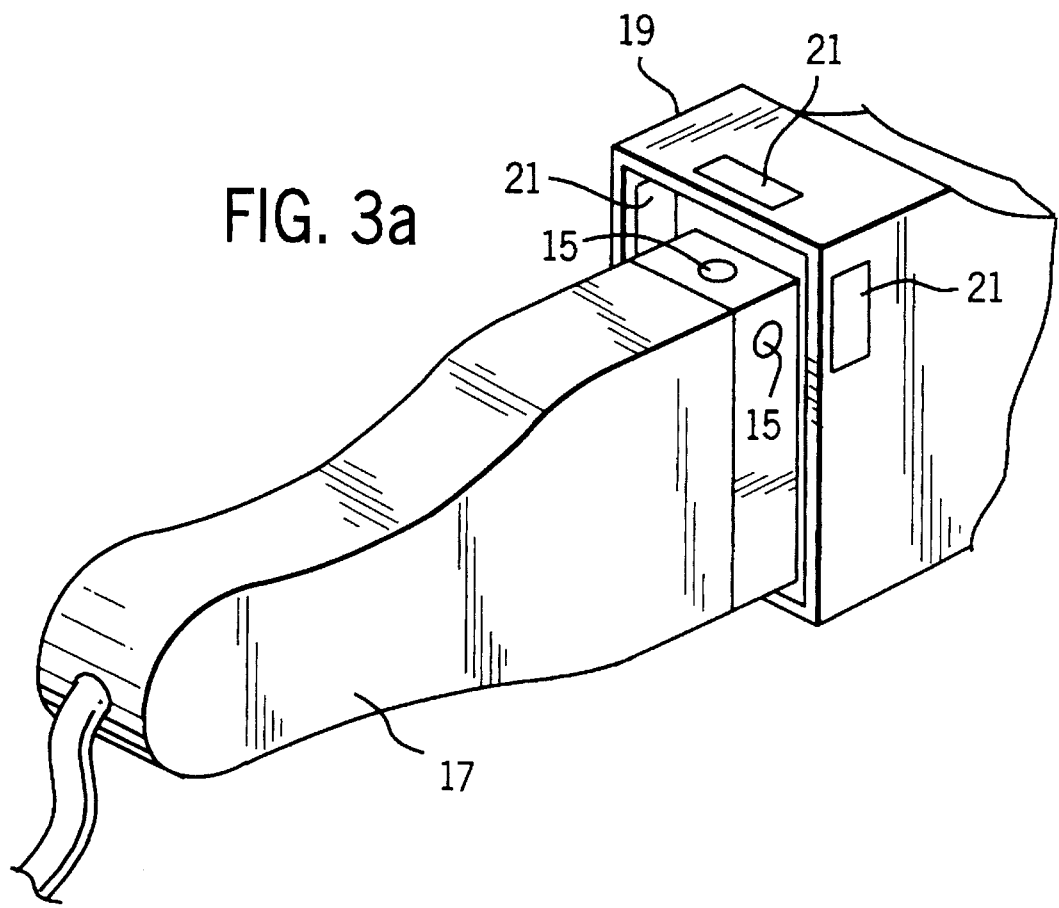
FIGS. 3a and 3b illustrate an exemplary bar code reader for a pumping channel of the FIG. 2 system.

The drugs normally are in liquid form in a drug container which is secured mechanically to a drug channel. A bar code which includes the drug name is included on a drug label. A bar code reader 17 is held manually as shown in FIG. 3a, or can be located internally within each drug channel pump. When the bar code reader 17 is placed in a vicinity of the drug container, the bar code reader electronically senses the bar code. Further, the pumping system can use a unique arrangement of electromagnetic Hall sensors and magnetic strips in each drug channel to determine which drug channel is currently being read so that the reading of the drug supply container can be tied to the appropriate drug channel.

Figure 3B:
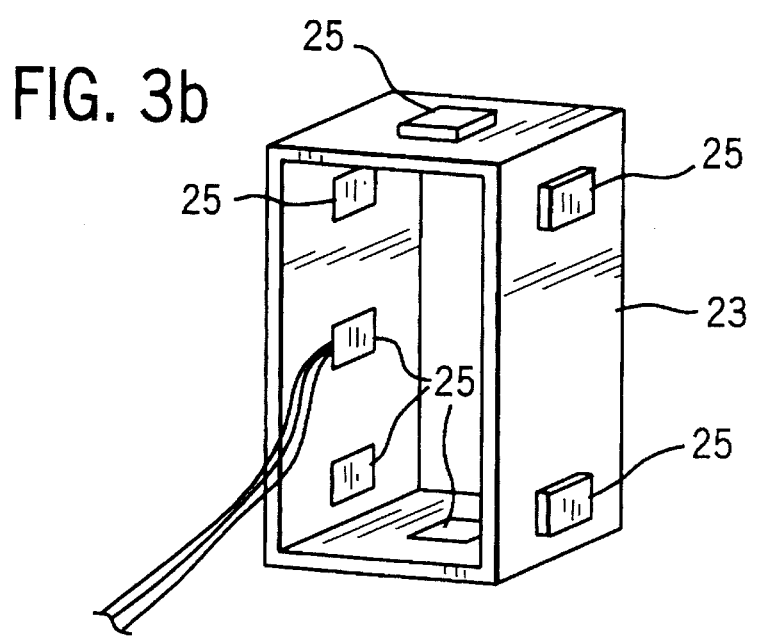

For example, in FIG. 3a, Hall sensors 15 on the bar code reader 17 detect the presence of magnetic strips 21 placed on a receptacle 19 of a drug channel. The bar code reader must be placed in a vicinity of the receptacle 19 to read a bar code on the label of a drug vial secured in the drug channel. FIG. 3b shows an alternate configuration of a receptacle 23 which completely surrounds an end of a bar code reader 17. In this embodiment, Hall sensors 15 are replaced by a magnetic strip around a perimeter of the bar code reader. The receptacle includes Hall sensors 25 mounted thereon to detect the magnetic strip located about the perimeter of the bar code reader 17.

The FIG. 2 host controller 2 operates displays 18 and peripherals (e.g., floppy disk drive 20 for disks 34, system bus interface 22 for bus 36, parallel printer interface 24 for printer 38, graphics display adapter 40 for display 18 and input/output (I/O) card 44). The host controller 2 also controls an A/D converter, a key lock switch, optional VGA compatible graphics, audio output circuitry, a timer circuit, non-volatile memory, battery backed static RAM memory for storage of non-volatile data (e.g., drug information stored in a drug table) and dynamic RAM. Power supply 42 is provided for the FIG. 2 system.

The host controller 2 can set the audio volume of an audio output signal to be one of a plurality of selected volume levels. In a preferred embodiment, eight separate volumes are provided. However, the number of selected volume levels can be greater or lesser than the number of volume levels selected for the preferred embodiment. The audio output signal is used to provide warnings or alarms to the user for when a failure, malfunction, or other alarm condition occurs within the FIG. 2 system.

Figure 4:
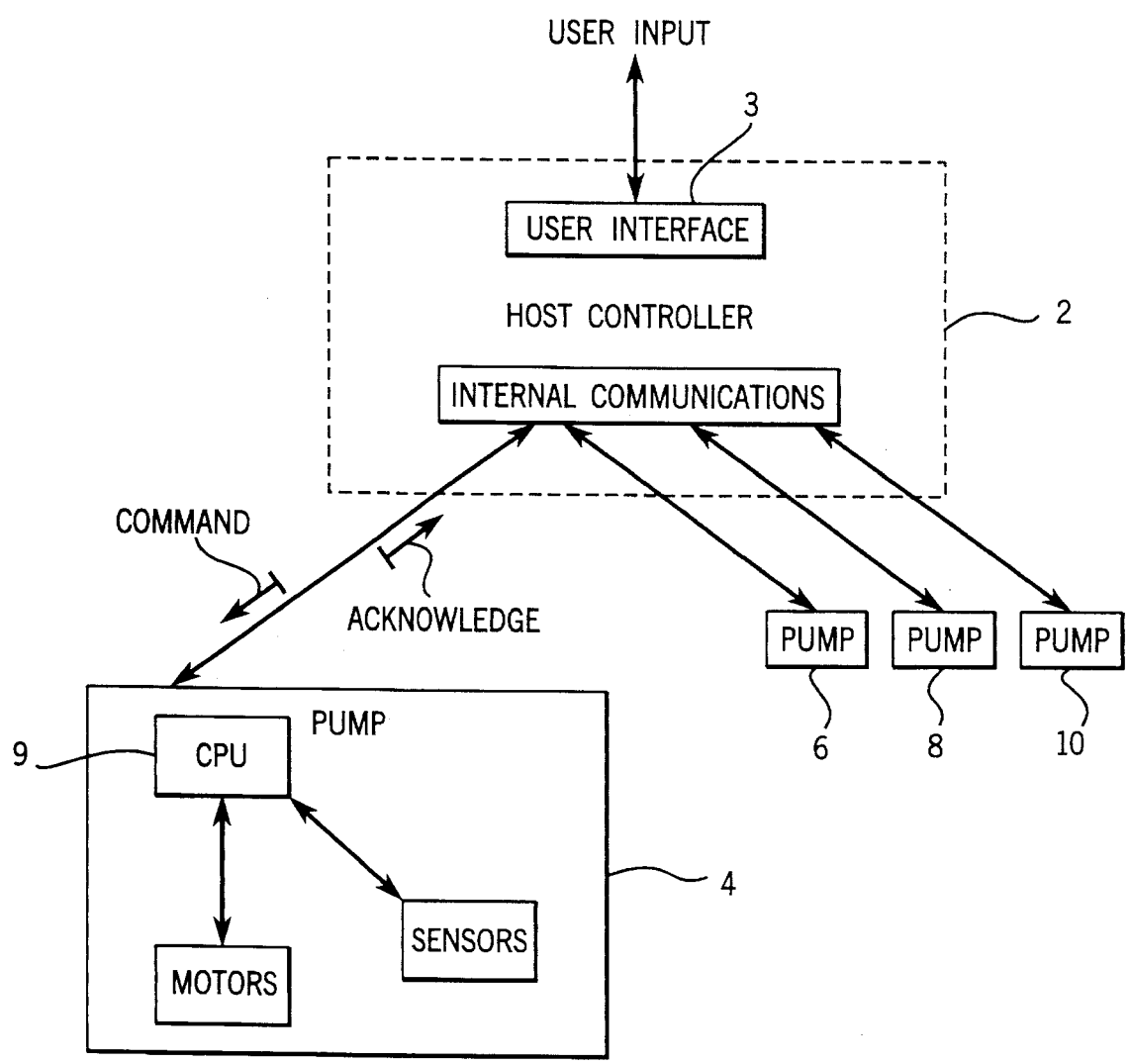
FIG. 4 is a diagram displaying system and channel communication between the user, the host controller and the independent pumping channels of the FIG. 2 system.

The host controller 2 sends commands to an independent controller 9 (i.e., CPU) for each of the drug channels (4,6,8) and fluid channel 10 shown in FIG. 4. For example, these commands include signals to stop pumping, set rate or dose, prime a drug channel, change pumping rate, read dose, initiate a backprime, start a pumping operation, perform a fluid prime, change fluid pumping rate, and read a dose from the fluid channel. In addition, the host controller 2 receives responses and cases from each of the pumps.

The independent controller 9 for each drug channel controller controls and monitors pumping from drug vials, provides automatic priming of drug sets in response to host controller 2 commands, and communicates status, alarm and error conditions within a drug channel to the host controller 2. The independent controller for a fluid channel controls and monitors pumping from fluid containers, provides automatic priming of fluid lines in response to host controller 2 commands, and communicates fluid line status, alarm and error conditions to the host controller 2.

The three drug channel modules are based on the known LifeCare 5000, and the fluid pump module is based on the known LifeCare 175, both available from Abbott Laboratories, Inc. The independent controllers of the drug and fluid channels are independent microprocessors which communicate to the host controller 2 through a communication link. Because the drug and fluid channel modules are, for the most part, known modules which do not themselves constitute a portion of the present invention, only features of these modules necessary for understanding the present invention will be provided.

A user interface provides a connection between various pumping channel controllers (FIGS. 1 and 2) and the user. This interface includes a user accessible panel which is divided into four regions: three drug channel regions, each directly beneath one of the three drug channel mechanisms, and one fluid channel region directly beneath the fluid channel. The user can access all functions of the FIG. 2 system via the interface at any time after power-up, with the exception of self-diagnostics, system administrator functions, and floppy drive use.

In the FIG. 2 embodiment, a touch screen 14 represents a module which is accessible to the user and controlled by the host controller 2. A key pad included on a host controller interface panel includes 16 front panel buttons in a preferred embodiment of the present invention. The panel can accommodate additional buttons if they are needed in alternate embodiments of the present invention, including several hidden buttons. Both an identity of a button being depressed and its state are read by the host controller 2.

The buttons which control drug delivery to a patient remain visible on the interface panel during the entire time delivery is occurring or is possible on that drug channel. The user is therefore not required to exit a current function to start or stop drug delivery. The drug name, current delivery rate, dose or a setpoint of the PK model, and a pumping activity indicator are displayed for each drug channel on the interface panel.

The portion of the user interface located beneath the fluid channel mechanism includes a five digit display to identify delivery rate or total value delivered. LEDs are also included on the user interface panel to identify a power-on condition and to indicate when the system is running on battery power.

The host controller 2 provides channel set up functions for each of the drug channels 4, 6, 8 and fluid channel 10 shown in FIG. 2. This includes automatic identification and channel association of drugs placed in each drug channel and overseeing automatic priming of the drug and fluid channels. In addition, the host controller 2 provides drug and fluid delivery functions, system maintenance functions, data storage functions and handling of exceptional cases (e.g., malfunctions and alarm indications to the user).

The drug identification feature is implemented during a drug channel set up, after the host 2 is notified by an independent controller 9 that a drug channel door has been closed with a drug cassette in place. At that time, the host controller 2 prompts the user to scan a bar code included on a drug vial label. For the host controller 2 to accept the scan as valid, the bar coded label must be accessible to the bar code reader. The bar code reader remains active as long as a drug channel door has been closed with a cassette in place and the associated bar code label has not yet been successfully scanned.

As described previously, two sensors provided in each channel indicate the presence or absence of the bar code reader directly in front of that channel. The drug vial to be scanned must be properly positioned in a drug channel to be identified by the bar code reader, otherwise its label will not be recognized by the system.

After a drug has been loaded into a drug channel and a valid bar code has been read and the drug name has been recognized, the host controller 2 displays the name of the drug on a host display position below the drug channel receiving the drug vial. Once the bar code reader identifies the drug contained in a drug vial installed in a drug channel, the host controller 2 prompts the user to enter drug delivery information associated with that drug. The host controller 2 will not permit a drug channel to prime or pump any drug until the drug vial loaded into the channel has been successfully identified using the bar code reader.

A significant delivery function of the present invention is the ability to provide drug specific functions. For example, the host controller 2 allows the user to pick from allowed unit conversion sets specified for a particular drug being used. Unit conversion sets available for each drug are retained in the drug table of the host controller 2 memory. Drug delivery quantities in weight based units require entry of patient weight.

More particularly, after drug identification via the bar code reader, the host controller 2 displays all delivery control quantities (i.e., rate, dose and plasma level) using default units specified by a unit conversion set in the host controller's drug table for that drug, or, if preferred by the user, the units that were used during the most recent delivery of that drug. If other unit conversion sets are permitted for that drug, the host controller 2 permits the user to select one. Afterwards, all quantities are displayed using the new units for rate, dose and plasma level specified by the new unit conversion set.

As mentioned above, one of the primary functions of the host controller 2 is to oversee drug and fluid delivery. With regard to drug delivery, the host controller 2 is designed to control infusion rate and bolus dose delivery or PK model-based drug delivery. The host controller 2 permits either bolus delivery or infusion delivery, but when both a bolus delivery and an infusion delivery are requested simultaneously, the bolus delivery takes priority, causing delay of the infusion delivery until the bolus has been completed.

For a bolus delivery, a bolus dose in units selected by the user must be input by the user before the start of delivery. The host controller 2 will only permit a bolus delivery to occur for drugs which have been identified in a drug table of the host controller's memory as being deliverable by bolus. To prevent accidental delivery, the user must confirm the request for a bolus delivery prior to starting delivery. In a preferred embodiment, the user can also select desired duration for bolus delivery ranging from default (i.e., the shortest time over which the drug can be delivered) to durations which are multiples of the default duration).

A bolus may be paused during delivery, after which the bolus may be resumed (i.e., causing the remaining dose to be delivered) or the bolus may be stopped, cancelling delivery of the remaining dose. No confirmation is required to resume a bolus once paused, and pausing does not affect the status of simultaneously delivered infusion delivery on the same channel.

Infusion delivery is only permitted for drugs which have been defined in the drug table as being deliverable by infusion. Continuous infusion requires that the user input a desired infusion rate and infusion units before the start of infusion delivery. A default value of infusion units is provided by host controller 2. The infusion rate is, in an exemplary embodiment, equivalent to a range of 0.1 ml/hr to 1200 ml/hr.

A PK model is maintained in the host controller's memory for all drugs that are listed in the drug table as having PK models. When delivery of these drugs is initiated, the host controller 2 starts a PK model to continuously predict the theoretical plasma level of the drug being delivered. The selected PK model allows the user to query the predicted plasma level of the drug in a patient at any time during its delivery. Again, PK model-based delivery is only permitted for drugs which have been so defined in the drug table of the host controller 2. The system can provide the user with predicted (theoretical) plasma levels (i.e., level of drug in patient bloodstream) when delivering drugs by bolus or continuous infusion because a background calculation of the theoretical plasma level is continuously updated.

Before initiating a PK model-based delivery, the user must input a plasma level set point in user selectable units. The host controller 2 will not accept a plasma level set point greater than the maximum plasma level defined in the drug table for that drug. Further, PK delivery cannot be initiated until certain patient parameters, such as weight, have been confirmed by the user. Upon initiation of a PK delivery, the host controller 2 displays setpoint plasma level in user selected units, the predicted (theoretical) plasma level in the same units, and the infusion rate in default units throughout the entire PK model-based delivery.

In the fluid channel 10, only continuous infusion is permitted. The user must enter a delivery rate (e.g., between 1 and 1200 ml/hr) before fluid infusion can be initiated. In an exemplary embodiment, only ml and ml/hr are used to define fluid rate and cumulative dose units.

A key feature of the present invention is its ability to handle incompatibility between drugs administered to a patient via the FIG. 2 system. For this purpose, the host controller 2 detects and informs the user of possible physical incompatibilities between drugs identified by the bar code reader. The host controller 2 allows the user to decide whether to allow the system to automatically handle incompatible drug pairs involving bolus delivery. If the user decides to let the system automatically handle the incompatibility, the host controller 2 provides a visible indication on those channels that an incompatibility exists and that it will be automatically handled.

On channels where compatibility handling is active, bolus deliveries are preceded by and followed by a flush delivery from the fluid channel. Once a flush delivery for an incompatible bolus is completed, the fluid channel reverts to its previous delivery rate. The volume of each flush delivery is added to the total fluid delivered during the current patient case and stored in memory of the host controller 2.

The host controller can be designed to handle incompatibilities in all infusion mode combinations. In the preferred embodiment, the host controller 2 does not provide special handling for infusions, PK deliveries, or for three incompatible drugs loaded into the system at the same time, on channels where compatibility handling is active. Rather, the host controller 2 informs the user upon identification of incompatible drug conditions. Further, a visual indication of any currently incompatible drugs is provided to the user.

For each drug loaded and identified on the FIG. 2 system, the user can view the current total amount of drug delivered from the start of delivery to a particular patient. This information is stored in the host memory and is continuously updated throughout the delivery. For each drug loaded and identified, the user can specify a maximum dose limit for the duration of delivery to the patient. Once reached, the user is informed, but pumping continues. The user dose limit is reset and disabled when the patient case ends.

The host controller 2 also includes a global stop which deactivates all 3 drug channels at once. Each channel must then be individually restarted to resume pumping.

Similarly, fluid specific functions are provided for the fluid channel 10. More particularly, the user can view the current total volume of fluid delivered to a patient from the beginning of the patient case. Further, the user can enter a maximum volume limit of fluid for each patient case. Once reached, the user is informed and fluid delivery is discontinued. The user volume limit is reset and disabled when the patient case ends.

The FIG. 2 host controller 2 also provides a plurality of system maintenance functions. These functions include a start up/shut down function, disk archiving function, configuration features, installation/security features, and system update.

The start up/shut down functions prevent drug and fluid delivery to a patient prior to user instruction to the host controller 2. The host controller 2 allows the user to end a current patient case only when no channel is pumping. Upon ending the patient case, the host controller 2 displays total volumes delivered and used for priming the administration set for each drug used, as well as total volume of fluid delivered and used for priming. These volumes are expressed in display units used at the time the patient case ended.

The disk archiving function of the host controller 2 stores event history and patient case information to floppy disk for later use and analysis. Configuration functions of the host controller 2 provide a means for the current date and time to be set.

At the user's option, access to certain functions of the host controller 2 is restricted and requires the use of a password. Once the password is successfully entered, the host controller 2 can be controlled to access an exception conditions log, an event history, user information, patient case information, and installation record/drug usage. Further, at the user's option, entry of this password can be required before information stored in the system can be transferred to the floppy disk. In addition, entry of the correct password can be used to control entry of information into the host controller's memory (e.g., hospital name, drug table updates and names of users allowed access to the system).

The password cannot be changed unless access to the system has been obtained, nor can the password be viewed unless access to the system has been obtained following accurate entry of the current password. Use of the password can thus be used to control access to a variety of features of the host controller 2.

As mentioned above, the present invention can provide data storage of event history, an exception conditions log, user information, patient case information, installation record/drug usage and drug tables. Event history data is stored by the host controller 2 as a chronological record of system cases associated with the FIG. 2 system alarms, malfunctions, and user interaction with the system. The event history data is stored in the non-volatile host controller's memory, and can be viewed by the user.

In an exemplary embodiment, the host controller 2 can store all cases that occur over a period of 7 days of continuous use. Once the case buffer is filled, old cases are discarded as new cases occur. The host controller 2 permits the user to disable and enable event history recording, and when disabled no subsequent cases are stored in the event history portion of the host controller's memory.

Exception conditions are stored by the host controller 2 as a chronological record of at least the last 30 exception conditions (i.e., malfunctions and alarms) applicable to the entire FIG. 2 system. Again, this log is stored in a non-volatile area of host controller's memory. Pumping channel exceptions are not stored in the individual pumps, but are stored as data in this portion of host controller's memory. Exception data is recorded automatically and cannot be disabled or erased by the user.

The host controller 2 also stores user information. This information includes, for example, up to 100 alphanumeric user IDs in a non-volatile area of host controller's memory.

Patient case data can, in an exemplary embodiment, be retained on the last 50 patient cases. The host controller 2 allows the user to optionally store a patient ID as well as other information on age, sex, and weight. The patient weight can be input and displayed in pounds or kilograms.

For each patient case, the host controller 2 stores the user ID of the user who ended the patient case, the total number of users who identified themselves to the system during the patient case, the time the patient case started, and the duration of the patient case. The host controller 2 also records the number of drugs delivered during the patient case, the total volume delivered and total volume used in priming for each drug used during the patient case, as well as the total volume of fluid delivered and total volume used in priming. This information is expressed in display units currently being used at the time the patient case ended.

Installation record/drug usage data is retained by the host controller 2 and includes information regarding the installer's name, the site name, installation date and information pertaining to specific hardware configuration of the FIG. 2 system.

Drug table data is also stored by the host controller 2. The drug table includes information (e.g., drug incompatibilities, suitability for bolus infusion delivery or PK delivery, PK model-based input parameters and maximum allowable infusion rates, bolus doses, and theoretical plasma levels) for each drug as described previously.

Another key feature of the present invention is its ability to handle exception conditions. More particularly, when a malfunction, audible alarm or audible warning occurs, audio signal is emitted by the host controller 2 to alert the user. This audio signal is only discontinued when the user has acknowledged the condition, but may be temporarily stopped using a silence alarm button on the host controller interface panel. When a non-audible alarm or non-audible warning occurs, a discrete audio signal is optically generated to alert the user.

The host controller 2 detects malfunctions in the FIG. 2 system. Malfunctions which are identified by the host controller 2 and communicated to the user include signals indicating that a fluid or drug channel is unavailable due to an internal malfunction, indication that the system is unavailable due to a malfunction, and indications that the disk drive or other peripheral components are unavailable due to a malfunction.

The system can be configured to require presence of a drop detector in the fluid channel. When so configured, the host controller 2 requires the user to discontinue fluid channel operation when an alarm indicating the absence of a drop detector occurs. The fluid channel cannot be restarted until the exception condition regarding absence of the drop detector is rectified.

Alarms associated with the fluid delivery channel 10 include, for example, indications that the fluid channel autoprime mechanism has failed, that there is air in the fluid channel line, that the fluid channel door has been opened while pumping or that the fluid channel bag is empty. When fluid is unavailable, the host controller 2 allows the user to stop the fluid channel 10 and enter a new pumping rate, but the fluid channel 10 cannot be restarted until the exception condition is rectified. Alarms are also generated when there is a proximal occlusion or distal occlusion in the fluid channel pump, when there is a pressure error in the fluid channel 10, when the fluid channel volume limit is reached. In a preferred embodiment, the foregoing alarms are the minimum alarm conditions provided. Those skilled in the art will recognize that any number of alarms based on detection of any desired condition can be provided.

In a preferred embodiment, alarms associated with the drug channels 4, 6, 8 are, at a minimum, provided to the user when there is proximal or distal air detection in the drug channel cassette 13, when a channel door has been opened while pumping, when there is a proximal or distal occlusion in the cassette, when distal pressure is out of range, or when drug is unavailable. Non-audible alarms generated by host controller 2 include when AC power is not available or when the battery becomes discharged, failure to recognize a bar code, failure to associate a bar code with a channel, or alarms associated with floppy disk operation.

In a preferred embodiment, audible warnings (i.e., potential alarm condition) include, at a minimum, when the battery is low or when a drug container is near empty. Non-audible warnings include detection of excess air in an air trap chamber of a pumping cassette, loss of AC power or potential drug incompatibilities.

Drug and fluid channel status conditions are also continuously provided from the pumping channels to the host controller 2 for display. Status conditions which are displayed to the user via the host controller interface panel include, channel unavailable status, inactive status, autopriming status, backpriming status, testing cassette status, cassette test failure status, prime needed status, backprime needed status, prime verification needed status, infusion on hold status, bolus on hold status.

System status conditions which can be displayed via the host controller interface panel include: battery low status, security covers locked status, fluid channel unavailable status, drop detector missing status, volume limit reached status, disk drive unavailable status, patient parameters needed status, and user ID needed status.

As illustrated by FIG. 4, user interaction with the FIG. 2 system is via a user interface 3 in the host controller 2. Communication of commands, data, exception conditions, status and other information between the host controller 2 and drug and fluid channels is via the aforementioned serial communication link, capable of two-way communication. Communication is, for example, via packets limited to 30 bytes to ensure real time operation. Typical communications between the host controller 2 and pumping channels is via a command-acknowledgement loop. The host controller 2 (master) sends a command packet to one of the four pumping channel controllers 9 (slave), or vice versa. The targeted channel sends back an acknowledgement indicating receipt and initiation of appropriate action in response to the command.

Master-slave polling is used to detect synchronous communications between the host controller 2 and pumping channels 4, 6, 8 and 10. These synchronous communications include, for example, the aforementioned alarms and door open/door closed conditions. When, alarm conditions are sent from a pumping channel 4, 6, 8 and 10 to the host controller 2, the pumping channel awaits acknowledgement from the host controller 2. If an event is not acknowledged within a set time frame, the event is retransmitted until acknowledgement is received. After acknowledging the pump channel communication, the host controller 2 can either send a reset command to the pump or report failure to the user. For multi-event conditions, a pumping channel module will queue cases until all are acknowledged.

When multiple command packets are received or sent by the host controller 2, either the entire command packet is completed or the entire command packet is aborted. Thus, if an alarm condition occurs during execution of a multi-command packet, the partial command packet is not processed. Rather, the entire packet must be resent and executed in its entirety.

Where an illegal command is attempted, the command is ignored. An illegal command represents a command that cannot be processed at the time it is received. For example, when a drug channel 4, 6 and 8 is an unprimed state, a start command which is received cannot be executed.

A more detailed discussion will now be provided of the drug channels 4, 6 and 8. Each drug channel 4, 6 and 8 includes a pump which is preset at a position having an outlet valve closed, and an inlet valve open. A closed door switch is included in each drug pump to indicate when a drug channel door is closed with a cassette in place. An open door switch indicates that the drug channel door has been opened.

Pumping is accomplished in each drug channel via a pumping cassette which includes one or two proximal (inlet)

lines and one distal (outlet) line. The pump includes a mechanical reciprocating plunger mechanism and a pumping cassette through which the drugs are pumped. The pumping cassette has a primary inlet port and a pumped-liquid outlet port. The primary inlet port is connected to a piercing pin for receiving drug from a vial. However, alternative drug containers and connection methods can be used. The cassette also includes a secondary inlet port which remains normally closed. However, if desired, the secondary inlet port can receive a second drug, or drug diluent, for mixing with drug which has been introduced to the cassette via the primary inlet port.

A principal function of the independent controller 9 in each drug channel is to control drug delivery, priming of the drug delivery line, communication with the host controller 2, error detection and error reporting within the drug channel. The principal activity of the drug channel is drug delivery, whereby liquid is moved from one of the cassette inlet lines to the outlet line. The inlet lines, referred to herein as primary and secondary inlets, are typically configured with the primary line connected to a drug vial, and the secondary line disconnected. An exemplary delivery range is from 0.1 ml/hr to 1200 ml/hr.

For each pumping cassette, the drug channel controller responds to user commands to control bi-directional flow. Bi-directional flow control is critical for autopriming. During autopriming, the host controller 2 instructs operation of the valve actuators and plungers in each drug channel to displace air from the drug cassette. Further, the autopriming sequence can be used for priming the output line to the patient.

Each drug channel receives commands directly from the host controller 2 via the serial communication interface at an exemplary data rate of 1200 baud. These commands include the aforementioned communications to set rate, start pumping and so forth. Each independent controller 9 detects anomalies within its own drug channel pumping line. Error conditions and significant cases are communicated by each channel controller to the host controller 2.

Three different priming operations are required for the drug channel: the drug channel can fill, with drug, a cassette which is full of air distal to the air trap chamber (i.e., completely empty cassettes, cassettes with air in the pumping bowl, and cassettes with air in the distal tubing); the drug channel can remove air introduced into the cassette air trap without moving it to the outlet line; and the drug channel can remove air trapped between the secondary inlet and an optional secondary reservoir. The drug channel detects errors and reporting is performed by the drug channel to the host controller 2 with respect to four classes of errors: electronic, mechanical, cassette and communication.

Electronic integrity verification concerns the microprocessor memory, A/D lines and other microprocessor board and sensory apparatus. Mechanical integrity verification concerns verifying the mechanical pumping system is moving in accordance with commanded operation via the use of position detection feedback on three stepper motors included in each drug channel. Cassette integrity verification ensures that a cassette introduced to a drug channel is capable of withstanding pressures associated with pumping without leaking and is not occluded. Communication error detection is necessary to verify that transmitted data is accurate in accordance with the serial communication protocol. All failures are transmitted by the drug channel to the host controller 2, and the drug channel will confirm that the host controller 2 is aware when an alarm condition exists.

More particularly, electronic integrity verification is used to verify electronic and software integrity. For example, on power-up, the drug channel performs a RAM test, a ROM test, an A/D converter test and a watchdog test. The drug channel verifies serial communication integrity by the ongoing existence of incoming message packets. The drug channel verifies integrity of the air sensor by ensuring an air signal is seen whenever the door is open.

Mechanical integrity verification to ensure safety, involves verifying an ability of the pump channel mechanism and cassette to pump accurately. These tests are performed before pumping, and if any test fails, the drug channel is not permitted to pump. Motor position check and re-synchronization tasks (if necessary) are performed prior to pumping (e.g., when the system is activated), and no maximum time requirements are associated with these tasks.

Another function of each drug channel (4,6,8) is to perform a cassette integrity test to check for static occlusion and valve leaks when a cassette door is closed with a cassette in place. Occlusion detection is performed via the proximal and distal pressure sensors (i.e., pressure threshold is exceeded on proximal or distal side), after which an occlusion alarm is reported by the affected drug channel to the host controller 2.

Leak tests are performed automatically whenever the cassette door is closed with a cassette in place. All of these tests are performed by monitoring pressure inside the cassette and are, for example, used to indicate the need for backpriming the cassette (automatic removal of air from the cassette done by pushing it back into the drug container) or to indicate that a bad cassette needs to be replaced. The proximal pressure sensor self-test is used to ensure that the pressure sensor stays within a desired operating range.

A priming function of each drug channel (4,6,8) removes air from the drug delivery set. A drug delivery set includes a pumping cassette, distal tubing, and vial adapter. Priming operations perform both proximal and distal occlusion detection.

A pumping function is initiated in response to a start pumping command after all integrity tests have been implemented and passed. During pumping, mechanical motor position flags are monitored continuously by optical sensors.

The pumping function of the drug channel provides for proximal occlusion detection and distal occlusion detection using proximal and distal pressure sensors, respectively. A distal air in line alarm and stop pumping signal are generated by a drug channel if an air bubble (e.g., greater than, for example, 100 µl) (microliter), occurs at the distal air detector. The pump will also generate a distal air in line alarm if, for example, 200 µl out of the last 2.0 ml of volume was air.

The pumping function also includes an empty container detection when cumulative amount (e.g., 200 µl) of air has entered the cassette from at least one inlet line. This cumulative total is reset whenever the cassette door is opened, or a priming operation is performed.

A door open detection mode of the drug channels 4, 6, and 8 is used to trigger return of the step motors in a given drug channel to a preset position. At all times except for electronic self-tests, (i.e., pumping, priming, and so forth), a "door opened" alarm is generated and transmitted to the host controller 2. After the door is opened, the drug channel retains pumping parameters (i.e., rate, dose limit, delivered dose) except for pressure limit. When the door is again closed, the drug channel retains all of these parameters until commanded to change by the host controller 2.

A description will now be provided of a fluid channel 10 control. A fluid pump within a fluid channel includes a plunger/inlet valve/outlet valve assembly and a DC motor to pump fluid.

The fluid channel controller 9 communicates with the host controller 2 via the serial communication interface to receive commands such as set rate, start and operational commands.

Like the drug channels, the fluid channel 10 detects anomalies in the pumping line and communicates error conditions and significant cases to the host controller 2.

The fluid channel 10 controls fluid delivery from inlet tubing to outlet tubing in an exemplary range of from 1 ml/hr to 1200 ml/hr. Further, the fluid channel 10 controls priming of air filled delivery tubing automatically. Like the drug channels, the fluid channel can detect four similar classes of errors: electronic, mechanical, fluid and communication.

Because pumping is the primary function of the fluid channel 10, various parameters are accessible by the host controller 2 to configure the fluid channel behavior during pumping cycles. These parameters include delivery rate, dose limit, drop detector, priming time limit and door closed flag. The drop detector parameter determines whether detection of an empty fluid container is required during the delivery cycle. This parameter can be selectively requested by the host controller 2. The priming time limit parameter provides fail-safe operation of the priming process. The door closed flag ensures that pumping and priming do not occur unless the delivery tubing is inserted and the pumping mechanism door latches closed. The flag is set whenever both the delivery tubing is inserted and the door latch is closed, and either a door opening or tubing removal will reset this flag.

Pumping functions of the fluid channel 10 include a priming cycle and a delivery cycle. Priming of the delivery tubing in response to a command from the host controller 2 consists of two phases: a proximal tubing filling phase and a distal tubing filling phase. During the proximal tubing filling phase, the fluid channel 10 activates its priming mechanism and starts pumping until a distal air sensor detects continuous fluid flow. After continuous fluid flow is detected, the priming mechanism is deactivated and control advances to a distal tubing filling phase. In the distal tubing filling phase, fluid is delivered at a specified delivery rate until the specified dose limit is reached as with a normal delivery cycle. The only difference is that when an air-in-line condition is detected during the distal tubing filling phase, the priming cycle returns to the proximal tubing filling phase instead of terminating the priming process.

Priming is discontinued when a specified dose limit is reached during the distal tube filling phase, upon receipt of a stop command from the host controller 2, upon expiration of a priming time limit, upon detection of an empty container by a drop detector, or by an alarm in response to error detection. During the delivery cycle, the fluid channel 10 delivers fluid from its proximal tubing to its distal tubing at the specified delivery rate, until stopped by the user or the user specified dose limit is reached.

Error detection is similar to that of the drug channels and includes electronic, mechanical and fluid integrity checks. An error detected by these tests results in stoppage of the pumping process and communication of the error to the host controller 2.

For example, electronic integrity verification includes use of a watchdog timer to interrupt the fluid channel CPU to ensure integrity of the fluid channel CPU, critical data storage verification, and sensor range verification with regard to temperature and power supply voltages. Mechanical integrity verification includes monitoring of motor slippage, monitoring of plunger motor shaft encoder slippage, pumping rate verification and motor voltage verification. Fluid integrity verification includes air-in-line detection, empty container detection, proximal occlusion detection, distal occlusion detection and differential distal occlusion detection (i.e., when average depositive pressure buildup of distal pressure, relative to the distal pressure at pumping start time, is detected). Detection of a drop detector (if required) and loss of the drop detector signal are also monitored.

It will be appreciated by those skilled in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A control system for use with an automated intravenous drug and fluid infusion system, said control system comprising:

plural pumping channels that operate independently for intravenously infusing drugs and fluid, each of said pumping channels having a pumping channel controller for independent delivery in multiple infusion modes; and a host controller that monitors and controls each of the pumping channels concurrently.

2. A control system according to claim 1, wherein said host controller receives signals generated within each of the pumping channels to identify a drug or fluid selected for use in that channel, and to control channel priming and delivery in response to the received signals.

3. A control system according to claim 2, wherein said host controller further includes:

a touch screen for user entry of control information, including drug dose and drug delivery rate for each drug pumping channel, and fluid delivery rate for each fluid pumping channel.

4. A control system according to claim 3, wherein said host controller further includes:

a display for displaying a selected drug, drug dose and delivery rate to the user for each drug channel, and for displaying fluid delivery rate for the fluid channel.

5. A control system according to claim 4, wherein each pumping channel control responds to commands from the host controller to perform pumping channel priming and delivery, and to signal error and status conditions of each pumping channel to the host controller, such that delivery of significant air to a patient is prevented.

6. A control system according to claim 1, wherein said host controller further includes:

a touch screen for user entry of control information, including drug dose and drug delivery rate for each drug pumping channel, and fluid delivery rate for each fluid pumping channel.

7. A control system according to claim 1, wherein said host controller further includes:

a display for displaying a selected drug, drug dose and delivery rate to the user for each drug channel, and for displaying fluid delivery rate for each fluid pumping channel.

8. A control system according to claim 1, wherein each pumping channel control responds to commands from the host controller to perform pumping channel priming and delivery, and to signal error and status conditions of each pumping channel to the host controller, such that delivery of significant air to a patient is prevented.

* * * * *